(12) United States Patent
Park et al.

(10) Patent No.: US 10,702,637 B2
(45) Date of Patent: Jul. 7, 2020

(54) GUIDING NEEDLE FOR SUCTION TUBE

(71) Applicants: INDUSTRIAL COOPERATION FOUNDATION CHONBUK NATIONAL UNIVERSITY, Jeonju-si, Jeollabuk-do (KR); CHONBUK NATIONAL UNIVERSITY HOSPITAL, Jeonju-si, Jeollabuk-do (KR)

(72) Inventors: Jong Kwan Park, Jeollabuk-do (KR); Jun Sung Park, Seongnam-si (KR)

(73) Assignees: INDUSTRIAL COOPERATION FOUNDATION CHONBUK NATIONAL UNIVERSITY, Jeonju-si Jeollabuk-do (KR); CHONBUK NATIONAL UNIVERSITY HOSPITAL, Jeonju-si Jeollabuk-do (KR); SUNGWON MEDICAL CO., LTD., Cheongju-si, Chungcheongbuk-Do (KR)

(*) Notice: Subject to any disclaimer, the term of this patent is extended or adjusted under 35 U.S.C. 154(b) by 506 days.

(21) Appl. No.: 15/539,751

(22) PCT Filed: Dec. 16, 2015

(86) PCT No.: PCT/KR2015/013774
§ 371 (c)(1),
(2) Date: Jun. 26, 2017

(87) PCT Pub. No.: WO2016/105014
PCT Pub. Date: Jun. 30, 2016

(65) Prior Publication Data
US 2017/0348467 A1 Dec. 7, 2017

(30) Foreign Application Priority Data
Dec. 26, 2014 (KR) .................. 10-2014-0190281

(51) Int. Cl.
*A61M 1/00* (2006.01)
*A61M 25/06* (2006.01)
(Continued)

(52) U.S. Cl.
CPC ......... *A61M 1/008* (2013.01); *A61B 17/3415* (2013.01); *A61M 1/00* (2013.01);
(Continued)

(58) Field of Classification Search
CPC ...... A61M 1/008; A61M 1/00; A61M 25/013; A61M 25/06; A61M 25/065;
(Continued)

(56) References Cited

U.S. PATENT DOCUMENTS 5,342,325 A * 8/1994 Lun .................. A61B 17/3415
604/272

FOREIGN PATENT DOCUMENTS

| JP | 10-052505 A | 2/1998 |
|---|---|---|
| JP | 2007-167482 A | 7/2007 |

(Continued)

*Primary Examiner* — Philip R Wiest
(74) *Attorney, Agent, or Firm* — Novick, Kim & Lee, PLLC; Jae Youn Kim

(57) ABSTRACT

The present invention relates to a guiding needle for a suction tube, which is for increasing accuracy and preventing medical accidents by enabling an operator to accurately recognize the bent direction of the needle and to stably hold the needle by means of a handle portion formed inside the rear end of the needle connected to a tube or by means of a separate fixing handle coupled to the inside of the rear end of the needle. In other words, the present invention relates to a needle having the rear end thereof coupled to one end of a tube connected to a drainage container for discharging body blood of a patient, wherein the needle has a coupling part formed inside the rear end thereof and comprises a fixing handle detachably coupled to the coupling part.

13 Claims, 17 Drawing Sheets

(51) Int. Cl.
  *A61M 27/00* (2006.01)
  *A61B 17/34* (2006.01)
  *A61M 25/01* (2006.01)
  *A61B 17/00* (2006.01)

(52) U.S. Cl.
  CPC .......... *A61M 25/013* (2013.01); *A61M 25/06* (2013.01); *A61M 25/065* (2013.01); *A61M 27/00* (2013.01); *A61B 2017/00455* (2013.01); *A61B 2017/00469* (2013.01); *A61M 25/0194* (2013.01)

(58) Field of Classification Search
  CPC .............. A61M 25/0194; A61M 27/00; A61B 17/3415; A61B 17/3417
  See application file for complete search history.

(56) References Cited

FOREIGN PATENT DOCUMENTS

| | | | |
|---|---|---|---|
| JP | 2010-063731 A | 3/2010 | |
| KR | 20-0467554 Y1 | 6/2013 | |
| KR | 10-1459313 B1 | 11/2014 | |
| WO | WO 98/23321 * | 6/1998 | ............ A61M 27/00 |

* cited by examiner

GUIDING NEEDLE FOR SUCTION TUBE

TECHNICAL FIELD

The present invention relates to a guiding needle for a suction tube, which is for increasing accuracy and preventing medical accidents by enabling an operator to accurately recognize a bent direction of the needle and to stably hold the needle when skin is penetrated, through providing a handle portion at an inward of a rear end of the needle connected to a tube, or through coupling a separate fixing handle to the inward of the rear end of the needle.

BACKGROUND ART

In general, patients who are undergone surgery develop complications if they do not immediately discharge unnecessary blood or exudates generated in the body, so that a medical suction unit called "Hemovac" or "Barovac" is used to forcibly discharge the blood or exudates.

As shown in FIG. 1, the medical suction unit is broadly divided into a drainage container 10, a needle 12 for penetrating into skin, and a tube 11 that connects the drainage container 10 to the needle 12. Among these, the needle 12 is bent by approximately 20° to 30°, so that the skin can be conveniently penetrated with the needle 12 by an operator who performs medical treatment.

However, since such a needle is formed of a metal material in a cylindrical shape, and the body fluid is put on a surgical glove during the surgery, the needle is very slippery, so that the needle is easily rotated when it goes out of the skin from the internal skin (surgical site). Thus, if the operator inadvertently rotates the needle in other directions, the bent end of the rotating needle may cause undesired damage on other important organs. In addition, since the bent direction of the end of the rotating needle is difficult to be visually confirmed by the operator from the outside, the operator may not predict the direction in which the needle proceeds, resulting in moving the needle in other directions, so that the undesired organ damage is caused in the body during the penetration process.

As a related art, there is Korean Utility Model No. 467554 ("Tube Fixing Clip of Medical Suction Unit") which proposes a configuration in which a through-hole into which a tube is inserted is formed in a central portion of a body, an opening is formed in one direction from the through-hole, and a plate body that is connected to the opening is formed at an outer surface thereof with a concave groove around which a suture thread is wound.

However, the above related art relates to a fixing clip for fixing a tube to the skin so as to prevent the tube from being separated from an affected area in a state that one side of the tube is inserted into the surgical site in the body after the needle connected to the tube penetrates into the body and then is removed therefrom, so that the related art may not solve a problem of organ damage caused by moving the needle in a direction undesired by the operator due to the rotation of the needle owing to the slipperiness that occurs when the needle initially penetrates into the skin.

DISCLOSURE

Technical Problem

An object of the present invention is to provide a guiding needle for a suction tube, which is for increasing accuracy and preventing medical accidents by enabling an operator to accurately recognize a bent direction of the needle through a fixing handle and to stably support the needle through a handle portion integrally formed at an inward of a rear end of the needle, or through a separate fixing handle detachably coupled to a coupling part provided at the inward of the rear end of the needle.

Technical Solution

According to the present invention, there is provided a guiding needle for a suction tube, in which the needle has a rear end coupled to one end of a tube connected to a drainage container for discharging body blood of a patient, wherein the needle includes a coupling part provided at an inward of a rear end of the needle, and a fixing handle detachably coupled to the coupling part.

In addition, the coupling part includes a coupling groove formed on an outer circumference of the needle, and a coupling protrusion is provided at an inner side of the fixing handle so as to be inserted into the coupling groove.

In addition, the coupling groove may include an elongated groove formed in a longitudinal direction of the needle.

In addition, the coupling part has one of circular, elliptical, and polygonal sectional shapes, and the fixing handle fitted to the coupling part has one of circular, elliptical, and polygonal inner sectional shapes corresponding to the sectional shape of the coupling part.

In addition, the fixing handle is divided into upper and lower bodies, has a hinge part on one side of the upper and lower bodies, and has a coupling-fixing device on an opposite side of the hinge part.

In addition, the coupling-fixing device may include magnetic members attractive to each other by a magnetic force.

In addition, the coupling-fixing device is formed in a latch shape so as to be latched.

In addition, the fixing handle has a coupling space into which the needle is elastically fitted through a coupling guide groove defined by opening one side of a single body of the fixing handle.

In addition, an antislip device is provided on upper and lower contact surfaces of the fixing handle.

In addition, the antislip device may include a plurality of concavo-convex parts.

In addition, the antislip device may include an adhesion layer having a surface coated with an adhesion material.

In addition, there is provided a guiding needle for a suction tube, in which the needle has a rear end coupled to one end of a tube connected to a drainage container for discharging body blood of a patient, wherein a handle portion is integrally formed with a predetermined inward portion of the rear end of the needle.

In addition, the handle portion may include a plurality of concavo-convex parts formed on a surface of the needle.

In addition, the handle portion may include an adhesion layer formed by applying an adhesion material to a surface of the needle.

Advantageous Effects

According to the present invention, the needle is prevented from being rotated due to the slipperiness of the needle and the inadvertence of the operator when the skin is penetrated, and medical accidents caused by the rotation are prevented in advance, by enabling the operator to stably support the needle through a handle portion integrally formed at an inward of a rear end of the needle, or through a fixing handle that can be easily attached and detached to the inward of the rear end of the needle.

In addition, a bent direction of the needle is accurately recognized by visually confirming the fixing handle coupled to the needle, so that the needle penetrating into the body can be moved in a direction desired by the operator, thereby positioning a blood discharge tube at an exact position.

BEST MODE

Mode for Invention

Hereinafter, preferred embodiments will be described in detail with reference to accompanying drawings. In the following description, when detailed description about well-known functions or configurations may make the subject matter of the disclosure unclear, the detailed description will be omitted.

Figure 1:
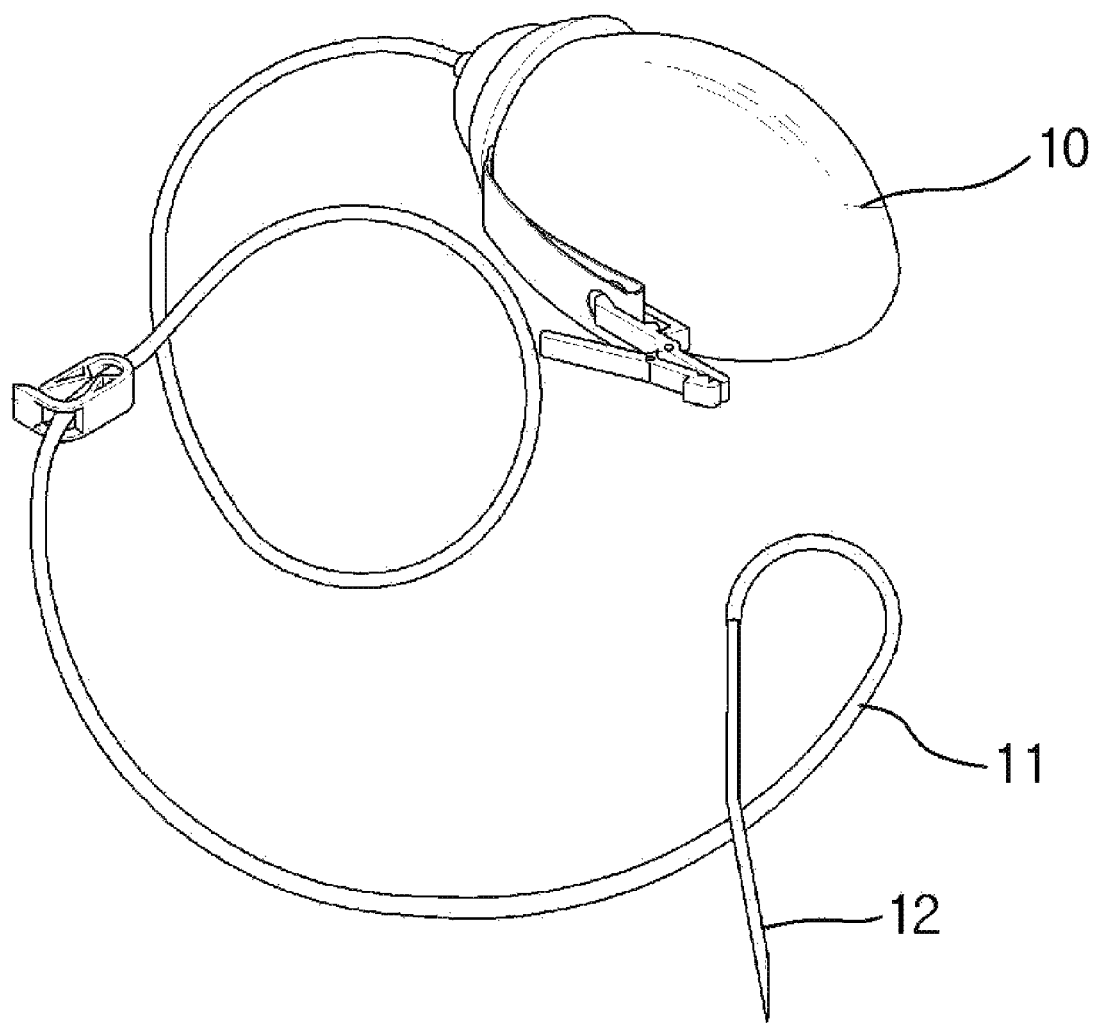
FIG. 1 is a perspective view showing a structure of a suction unit according to the related art.
Figure 2:
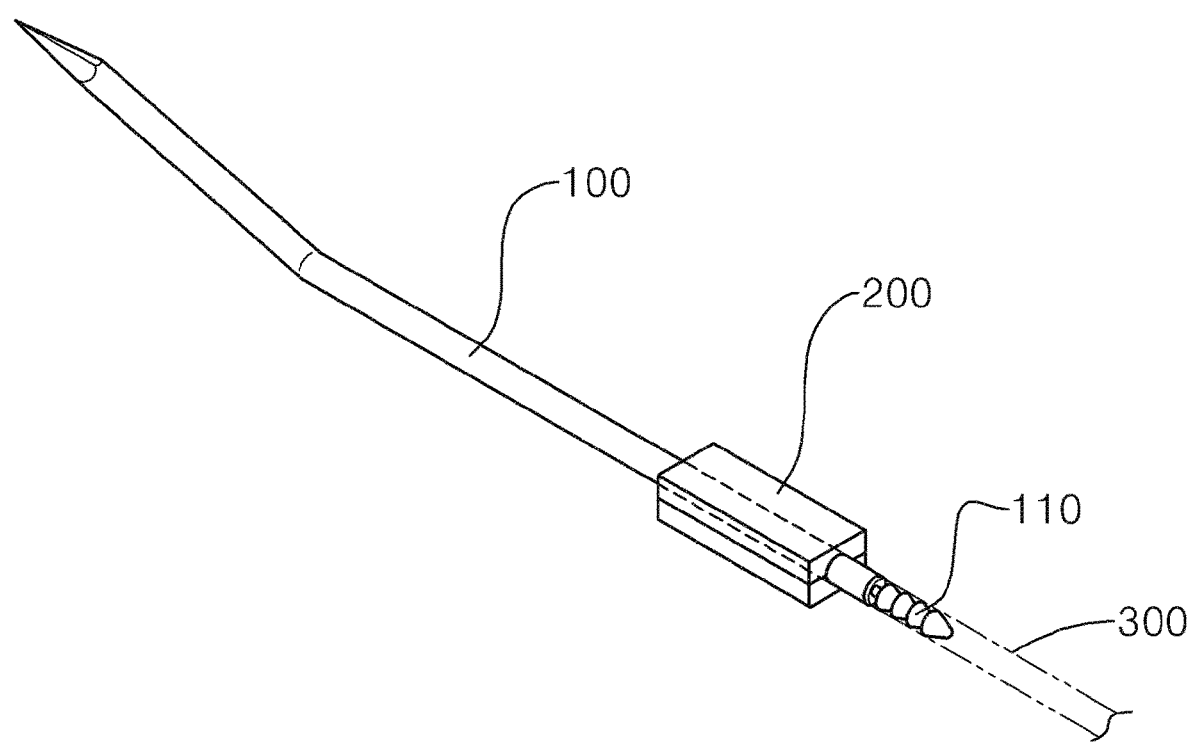
FIG. 2 is a perspective view showing a guiding needle for a suction tube according to the present invention.
Figure 3:
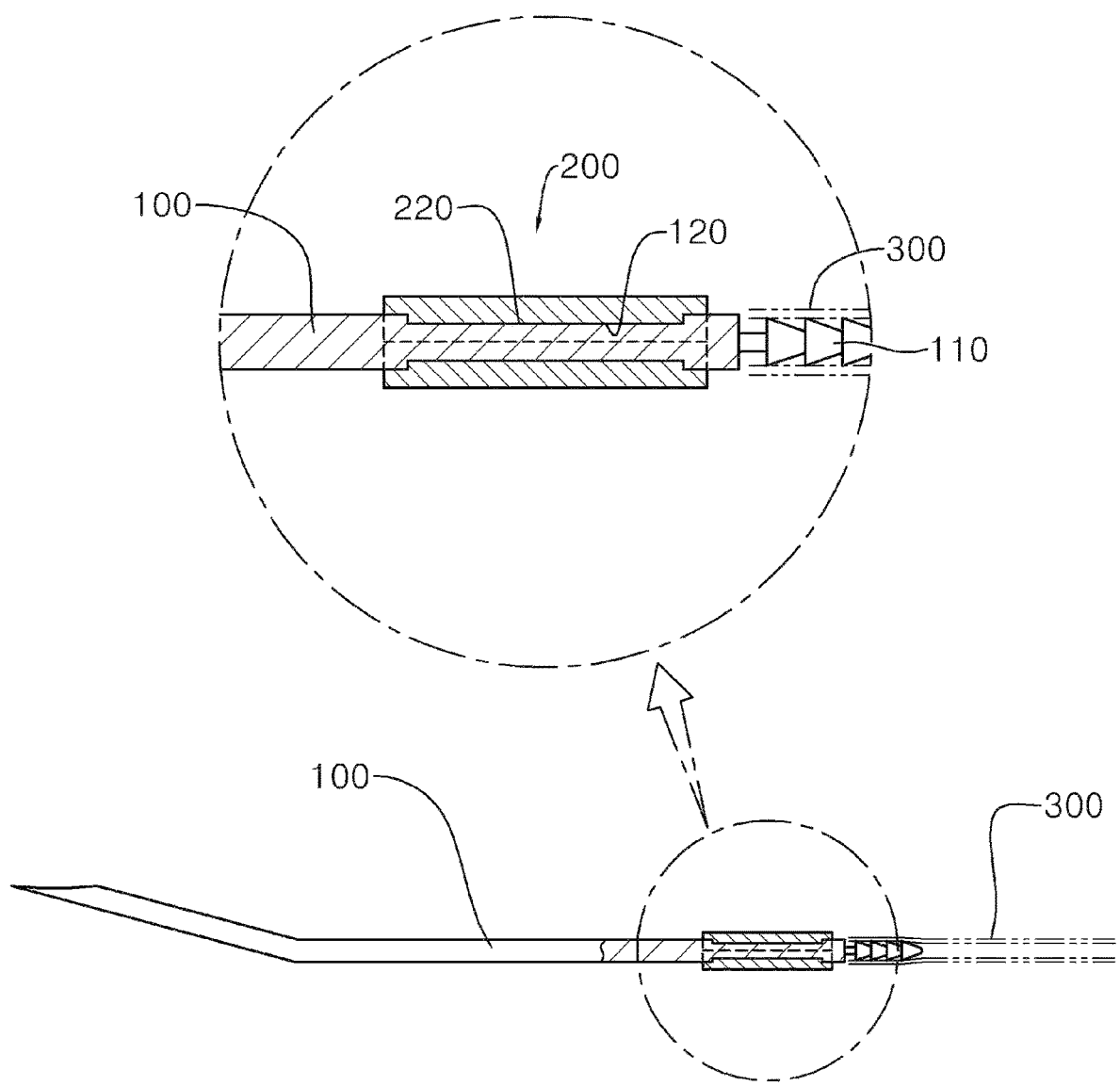
FIG. 3 is an enlarged sectional view showing the guiding needle for the suction tube according to the present invention.
Figure 4:
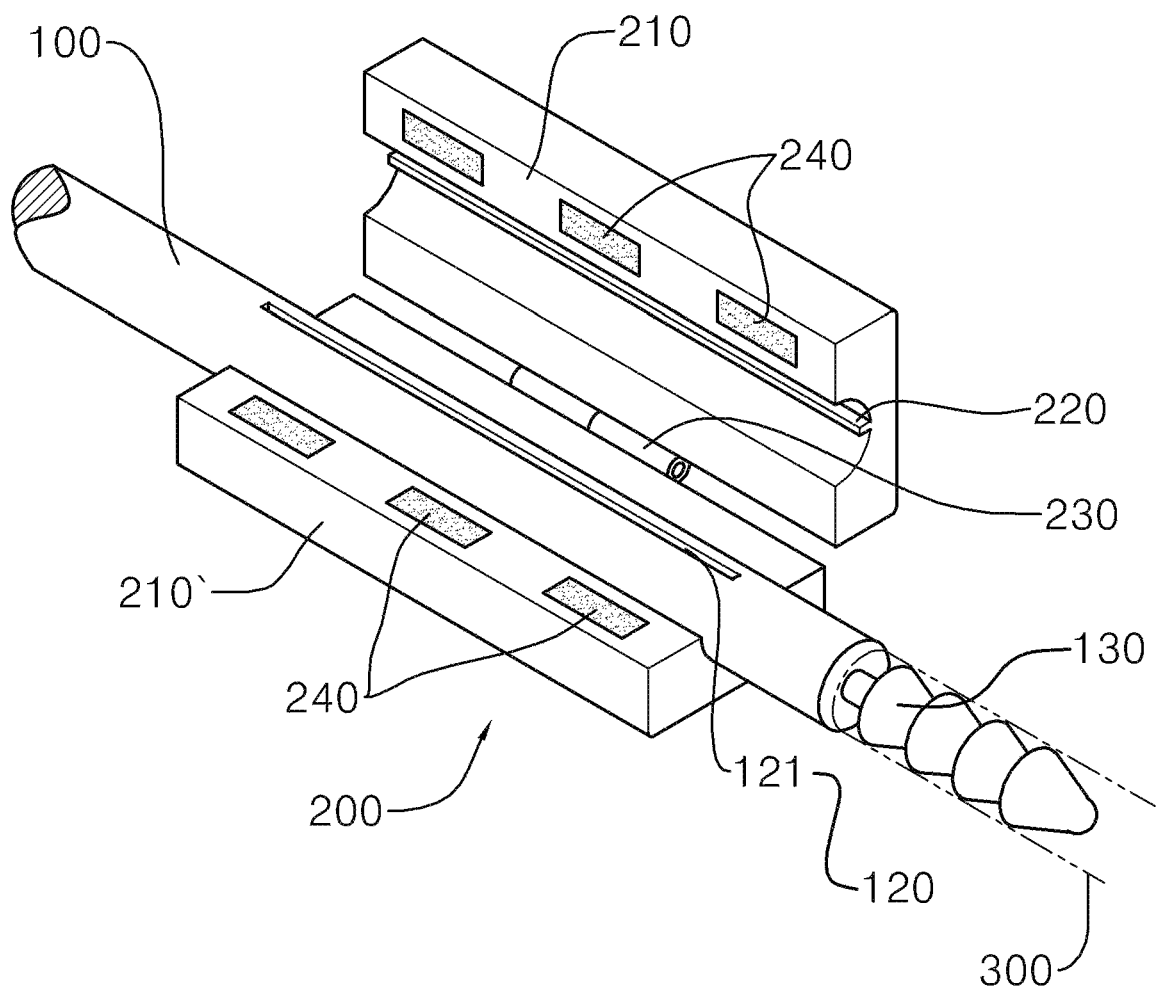
FIG. 4 is an enlarged perspective view showing a fixing handle and a coupling groove of the needle according to the present invention.
Figure 5:
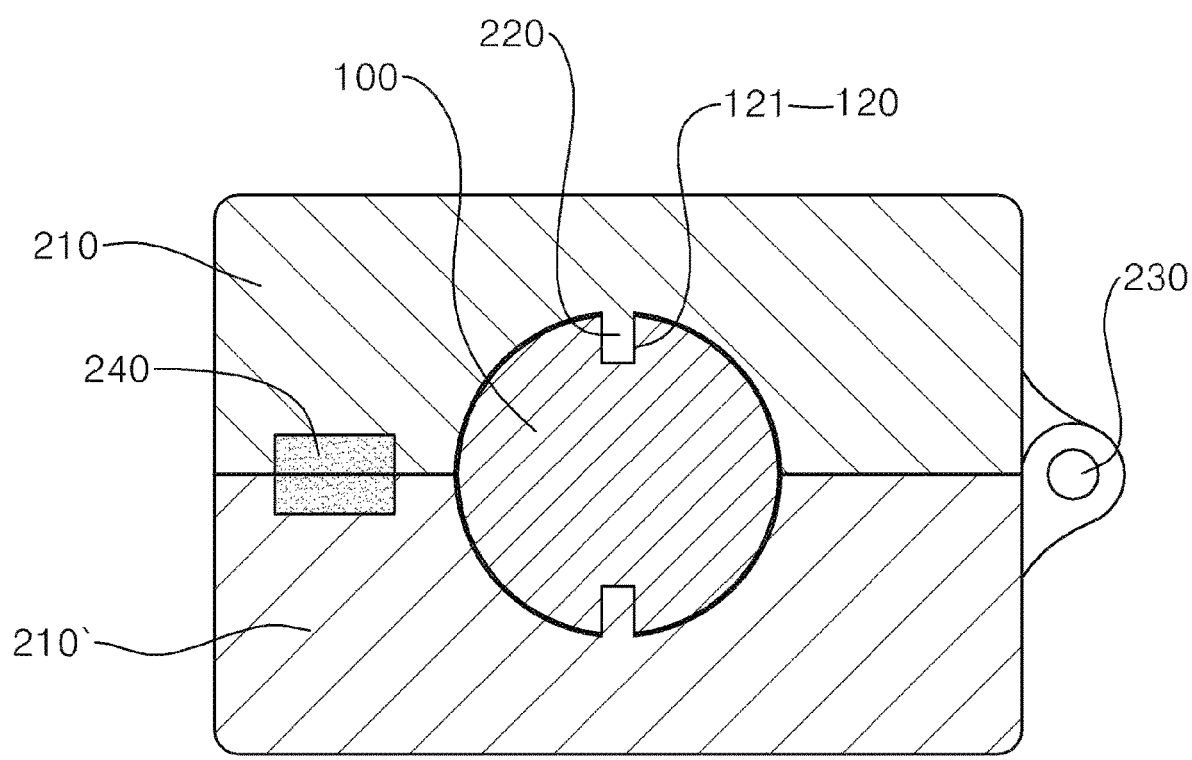
FIG. 5 is a sectional view showing a state that the fixing handle is coupled according to the present invention.
Figure 6:
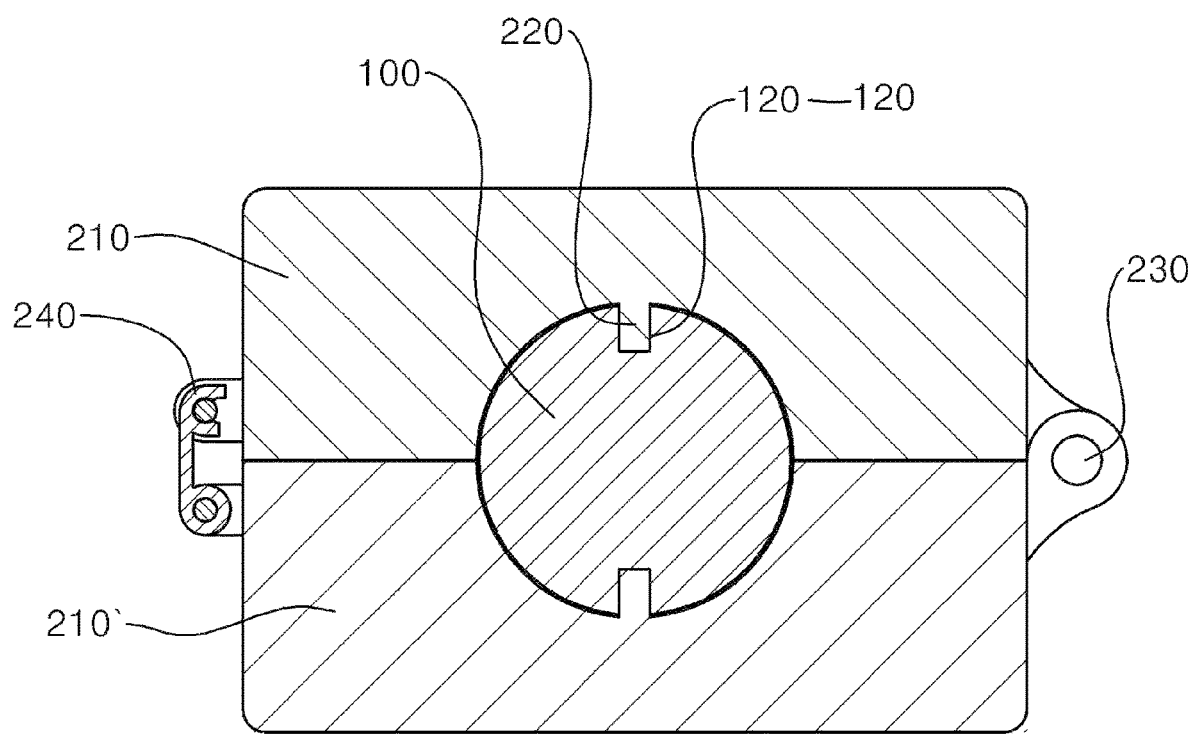
FIG. 6 is a sectional view showing a coupling-fixing device formed in a latch shape according to another embodiment of the present invention.
Figure 7:
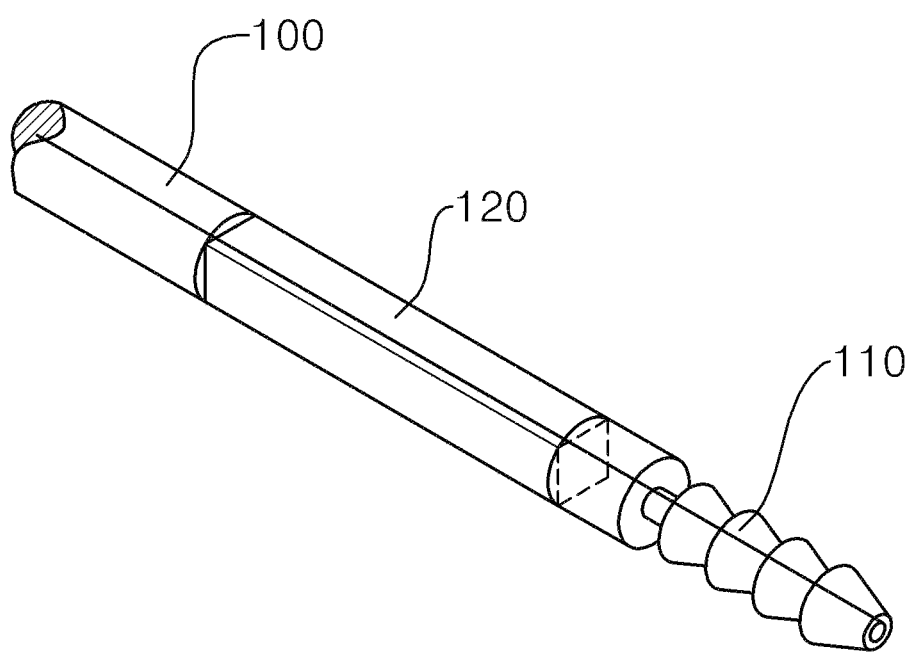
FIG. 7 is a perspective view showing a coupling groove formed in a polygonal shape according to another embodiment of the present invention.
Figure 8:
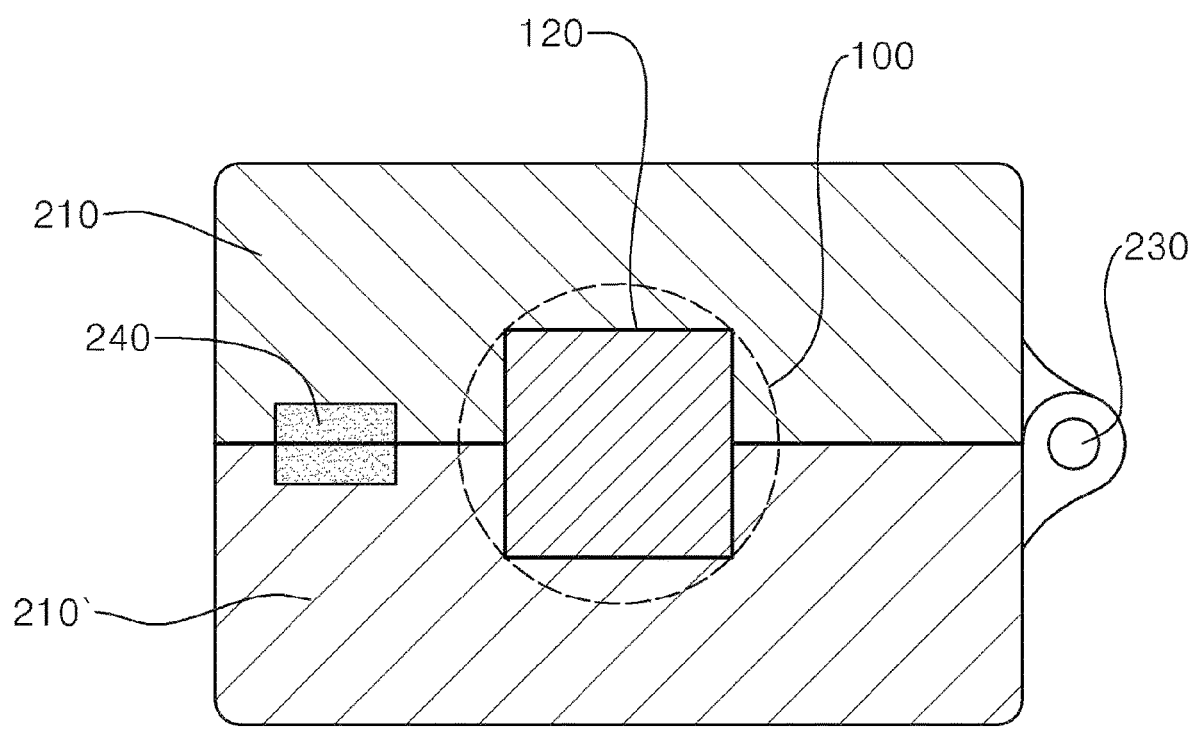
FIG. 8 is a sectional view showing a coupling state of the fixing handle according to the embodiment shown in FIG. 7.

The present invention relates to a guiding needle for a suction tube, which is used in a medical suction unit called "Hemovac" or "Barovac" which forcibly discharges unnecessary blood or exudates generated in the body after surgery. As shown in FIG. 1, which is a view of the related art, the medical suction unit includes a drainage container 10 for storing discharged blood, a tube 11, and a needle 12.

The needle 12 according to the related art is formed in a cylindrical shape, a part of the needle 12 is bent, a front end of the needle 12 is pointed, and a suction tube 11 is coupled to a rear end of the needle 12. The operator directly grips a portion of a body, which is located frontward from the rear end of the needle 12 by a predetermined distance, and pushes the needle 12 into the skin such that the needle 12 penetrates through the skin. At this time, the needle 12 has a cylindrical body having a small thickness, and the body fluid is put on a hand holding the needle, so that the needle 12 is slipped from the hand of the operator and easily rotated when the skin is penetrated. Accordingly, there is a problem that other tissues may be damaged, which will be solved through the present invention.

According to the related art, there is provided a guiding needle 100 for a suction tube, in which the needle 100 has a rear end 110 coupled to one end of a tube 300 connected to a drainage container for discharging body blood of a patient, wherein the needle includes a coupling part 120 provided at an inward of a rear end of the needle, and a fixing handle 200 detachably coupled to the coupling part 120.

The needle 100 is formed of a metal material in a cylindrical shape, penetrates into the skin with the rear end 110 fitted to the tube 300 so as to insert and guide the tube 300 into the body, and bent by approximately 20° to 30° for operational convenience of the operator. The rear end 110 to which the tube 300 is fitted is formed in a wedge shape so as to prevent the tube 300 from being easily separated, and a coupling groove 121 to be coupled to a handle is formed at an inward of the rear end 110.

The coupling part 120 is provided at a position spaced inwards from the rear end 110 of the needle 100 by a predetermined distance and formed around the needle 100 lengthwise along the needle 100, the coupling groove 121 is formed on an outer circumference of the needle, and a coupling protrusion 220 is provided at an inner side of the fixing handle 200 so as to be inserted into the coupling groove 121. At this time, the coupling groove 121 may be an elongated groove having a length of approximately 0.5 to 2 cm in the longitudinal direction so as to increase the coupling strength, or a plurality of short grooves may be formed in the longitudinal direction to obtain an effect similar to the elongated groove. In addition, the coupling groove 121 may be formed at upper and lower portions of the needle 100, or a plurality of coupling grooves 121 may be formed in a circumferential direction so as to increase the coupling strength.

In addition, according to another embodiment, the coupling part 120 may have one of circular, elliptical, and polygonal sectional shapes, and the fixing handle 200 fitted to the coupling part 120 may have one of circular, elliptical, and polygonal inner sectional shapes corresponding to the sectional shape of the coupling part 120. In other words, the coupling part 120 is preferred to have a coupling form that prevents rotation, and it is also a good example that the coupling part 120 is formed in shapes such as elliptical, square, hexagonal, and star shapes, as well as the circular shape.

As described above, the coupling part 120 may be modified into various shapes as the above examples. Since the coupling part 120 is formed as a groove that is inwardly recessed and not protrudes from the surface of the needle 100, the skin penetrated by the needle 100 is prevented from being damaged more than necessary.

The fixing handle 200 is fitted into the coupling groove 121 of the needle 100, so that the operator may hold upper and lower portions of the fixing handle 200 with a thumb and a forefinger, respectively, without directly holding and pushing the needle 100 into the skin such that the needle 12 penetrates through the skin, thereby stably gripping the needle 100. In addition, since the fixing handle 200 is easily detached and attached, the needle 100 may penetrate into the skin in a state that the fixing handle 200 is coupled to the needle 100. When the penetrated portion of the skin comes at the front of the fixing handle 200, the fixing handle 200 is conveniently removed, and then the needle 100 penetrates through the skin to the extent of the rear end 110 of the needle 100, so that the tube 300 can be placed in the body.

The fixing handle 200 is divided into upper and lower bodies 210 and 210', has a hinge part 230 on one side of the upper and lower bodies 210 and 210', and has a coupling-fixing device 240 on an opposite side of the hinge part 230. The hinge part 230 allows the upper and lower bodies 210 and 210' to be opened by rotating about the hinge part 230 so as to easily attach and detach the needle 100, and the fixing handle 200 is perfectly coupled to the needle 100 through the coupling-fixing device 240.

The coupling-fixing device 240 may include magnetic members provided at contact areas of the upper and lower bodies 210 and 210' so as to be attractive to each other by a magnetic force, or may be formed in a latch shape so as to allow the upper and lower bodies 210 and 210' to be coupled by the latch. Various other forms can be applied to the coupling-fixing device 240 as long as the upper and lower bodies 210 and 210' are fixed to each other while being easily detached and attached.

Figure 9:
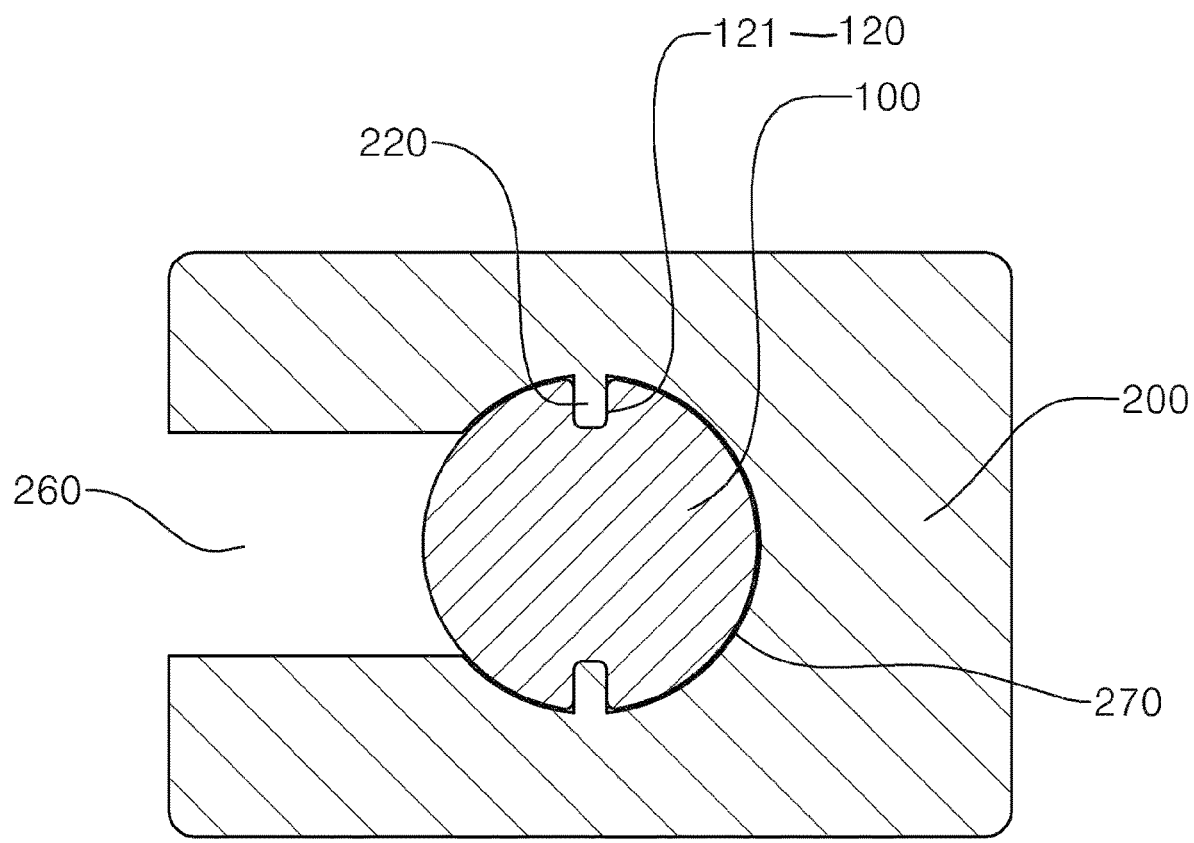
FIG. 9 is a view showing the fixing handle in the form of a single body according to another embodiment of the present invention.
Figure 10:
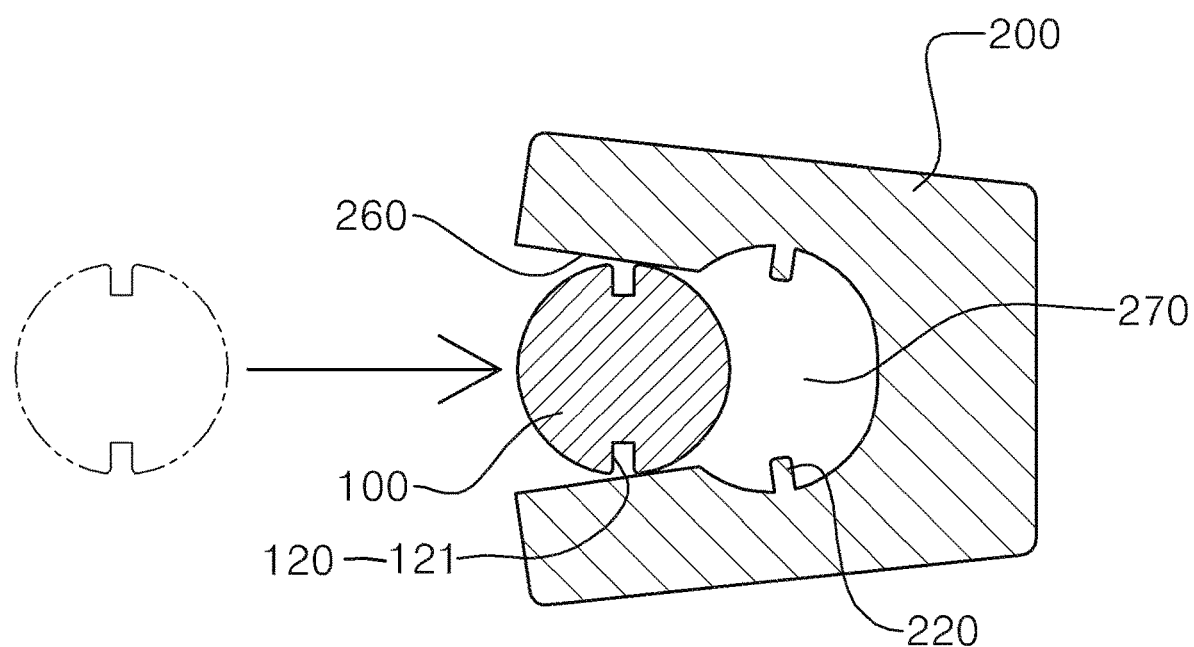
FIG. 10 is a view illustrating a process of coupling the fixing handle showing in FIG. 9.

In addition, according to another embodiment of the fixing handle 200, as shown in FIGS. 9 to 10, the needle 100 may be elastically fitted to a coupling space 270 through a coupling guide groove 260 formed on one side of a single body which is formed in a substantially "C" shape and having one open side. In other words, it can be coupled to the needle 100 through the elastic coupling without the hinge part 230 and the coupling-fixing device 240. The fixing handle 200 is preferred to be formed of a synthetic resin such as rubber or silicone to facilitate the elastic coupling.

Figure 11:
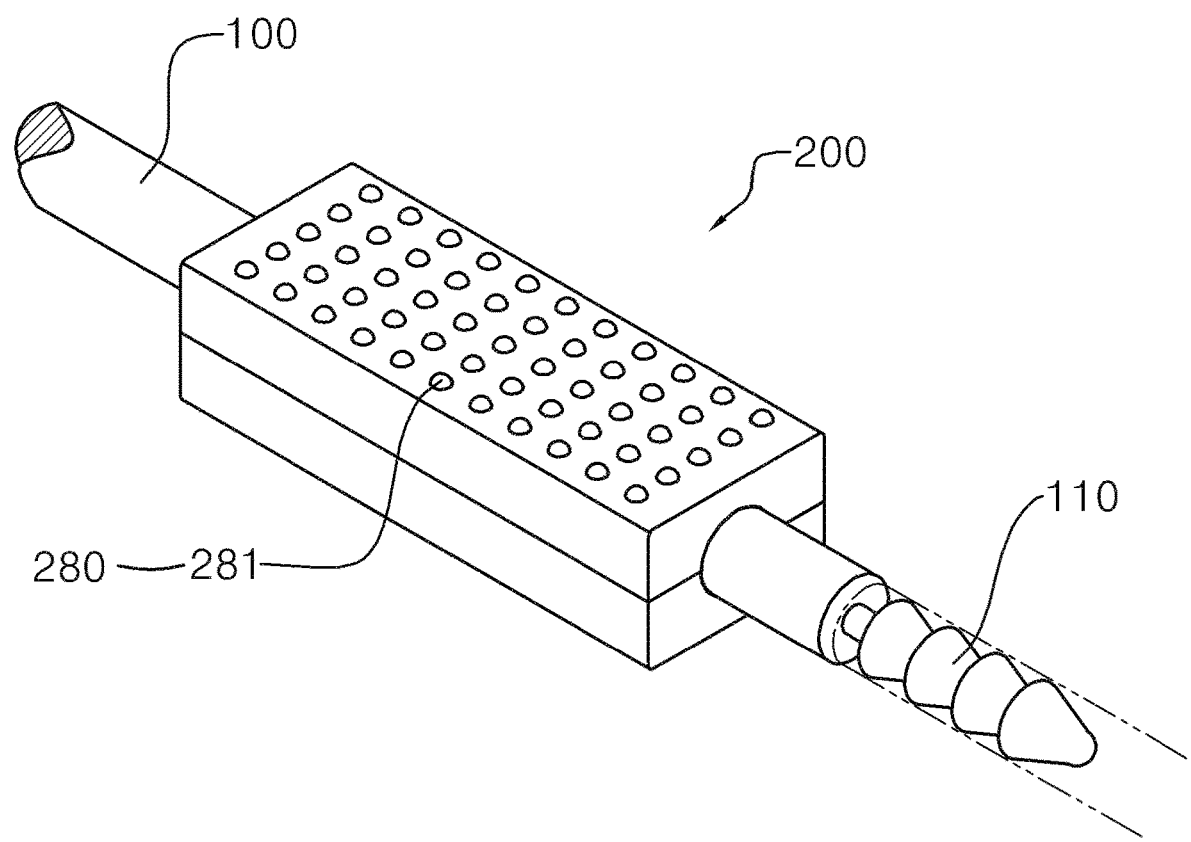
FIG. 11 shows an antislip device of the fixing handle having a concavo-convex part according to a first embodiment of the present invention.
Figure 12:
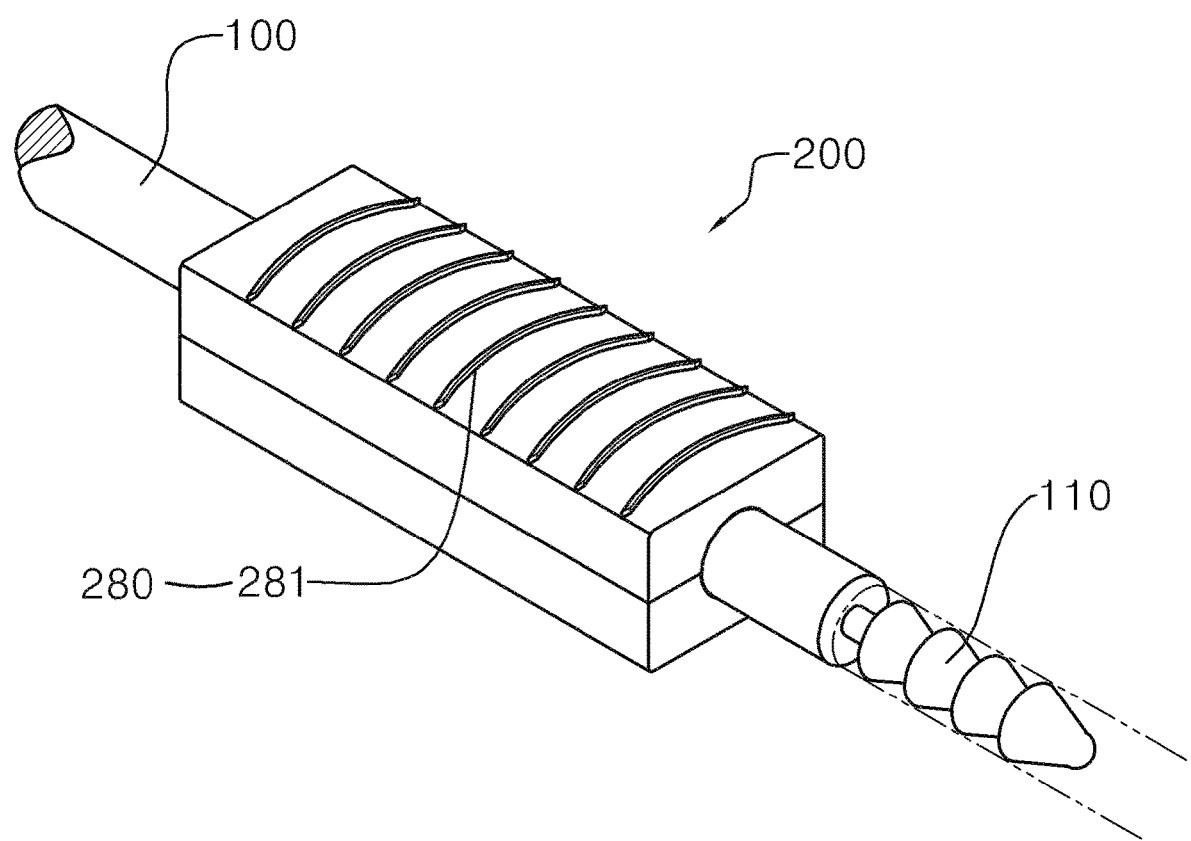
FIG. 12 shows the antislip device of the fixing handle having the concavo-convex part according to a second embodiment of the present invention.
Figure 13:
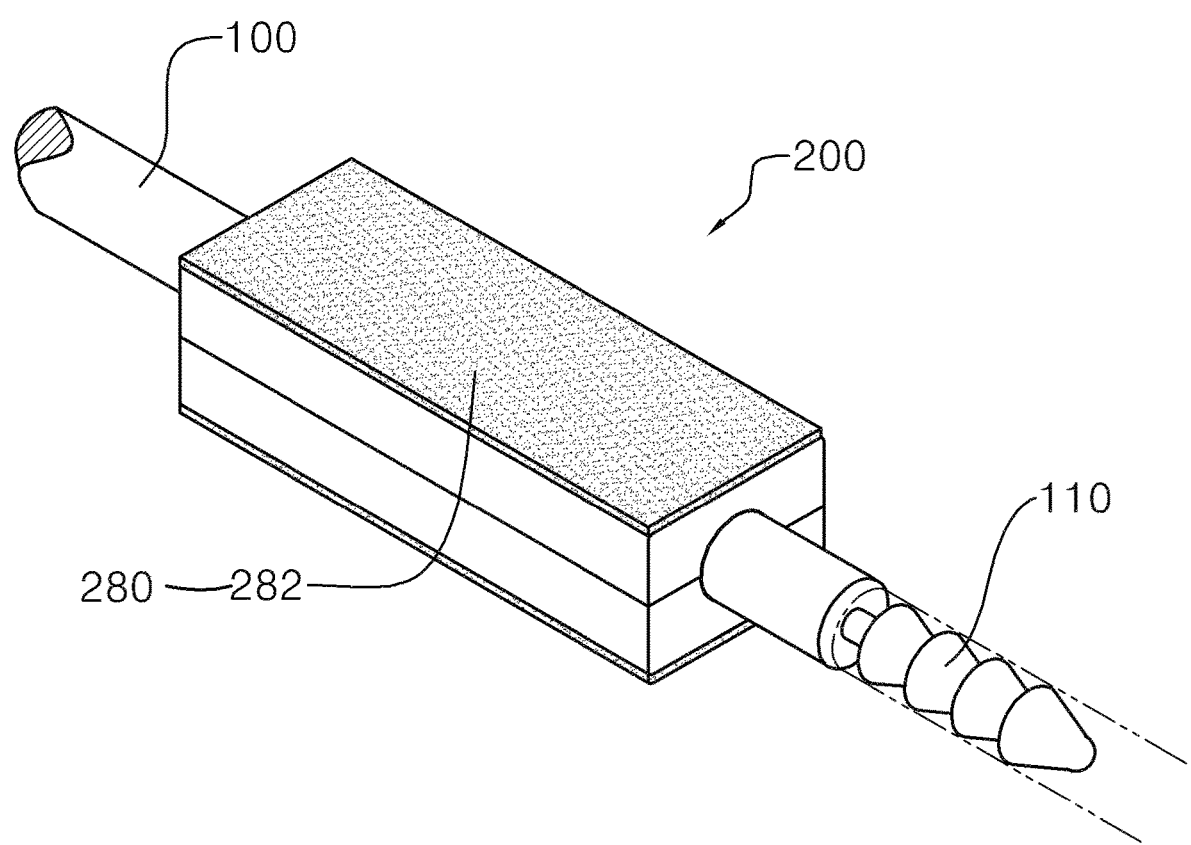
FIG. 13 shows the antislip device of the fixing handle having an adhesion layer according to a third embodiment of the present invention.

In addition, when an antislip device 280 is provided on the upper and lower contact surfaces of the fixing handle 200, the frictional force is increased at the gripping portion of the fixing handle 200, so that the hand of the operator is not slipped from the fixing handle 200, and can grip the fixing handle 200. The antislip device 280 may have a plurality of concavo-convex parts 281 arranged in the form of an embossed shape as shown in FIG. 11, or may prevent the slipperiness by a concavo-convex part 281 elongated in the transverse direction as shown in FIG. 12. In addition, as shown in FIG. 13, the slipperiness can be prevented in other forms through an adhesion layer 282 formed by applying an adhesion material.

In the present invention as described above, since the fixing handle 200 is completely fixed to the needle 100, if the bending portion of the needle 100 is directed upwards when the fixing handle 200 is initially coupled to the needle 100, it is possible to recognize the bent direction of the needle 100 penetrating into the body only by checking the handle, and the operator can move the needle 100 in a desired direction. In order to further facilitate the recognition, a display part (not shown) may be further provided on the fixing handle 200, so that the bent direction of the needle 100 can be easily and visually confirmed.

Figure 14:
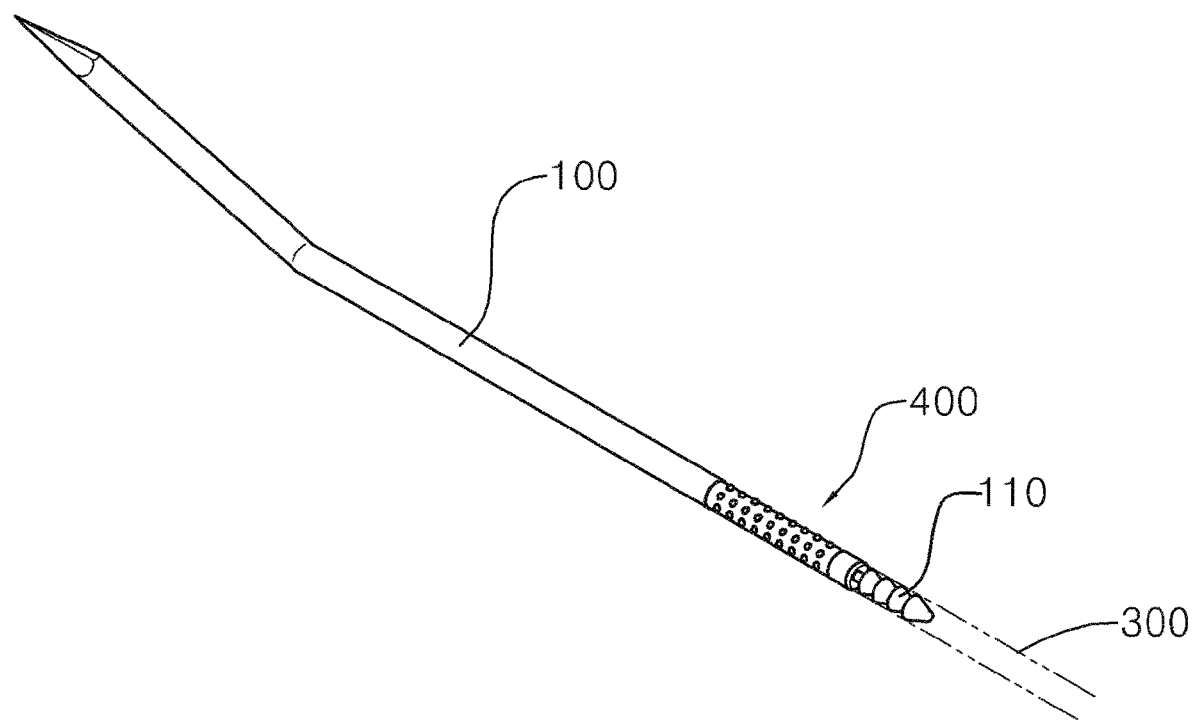
FIG. 14 is a perspective view showing a handle portion according to another embodiment of the present invention.
Figure 15:
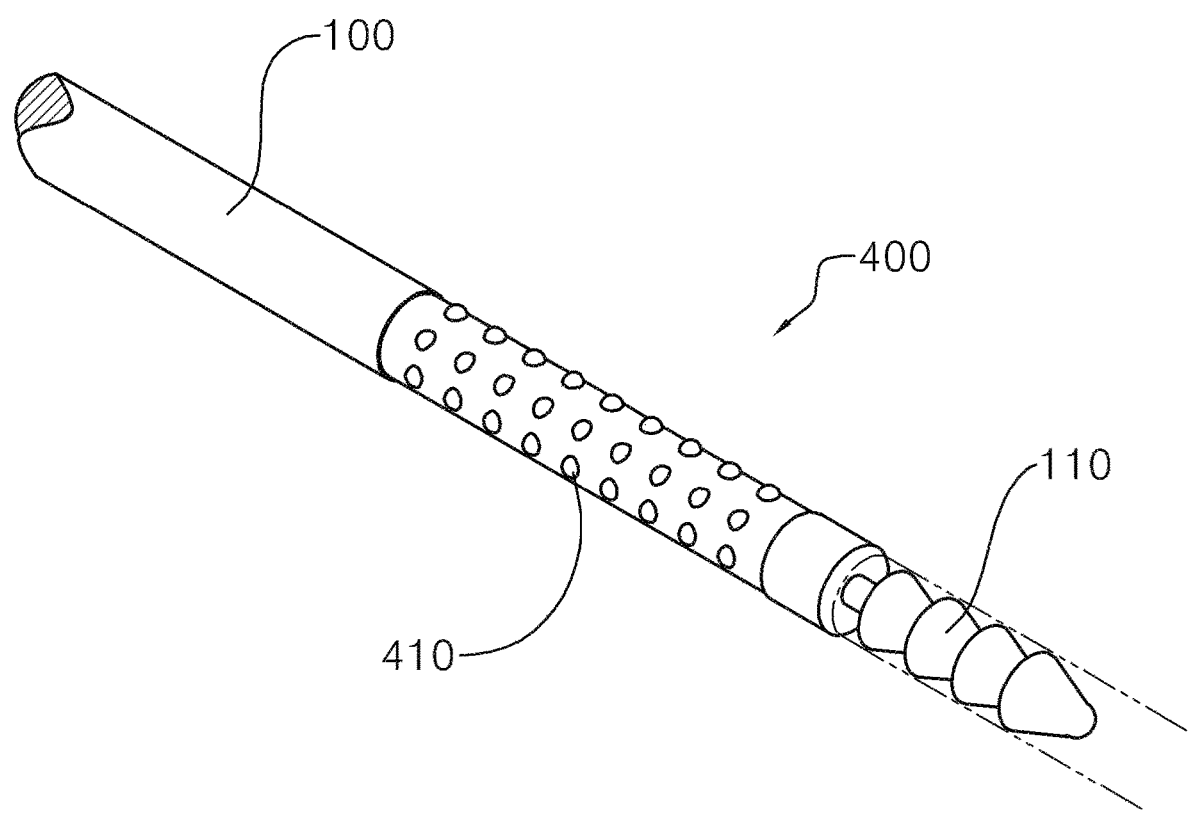
FIG. 15 shows the handle portion having a plurality of concavo-convex parts according to a first embodiment of the present invention.
Figure 16:
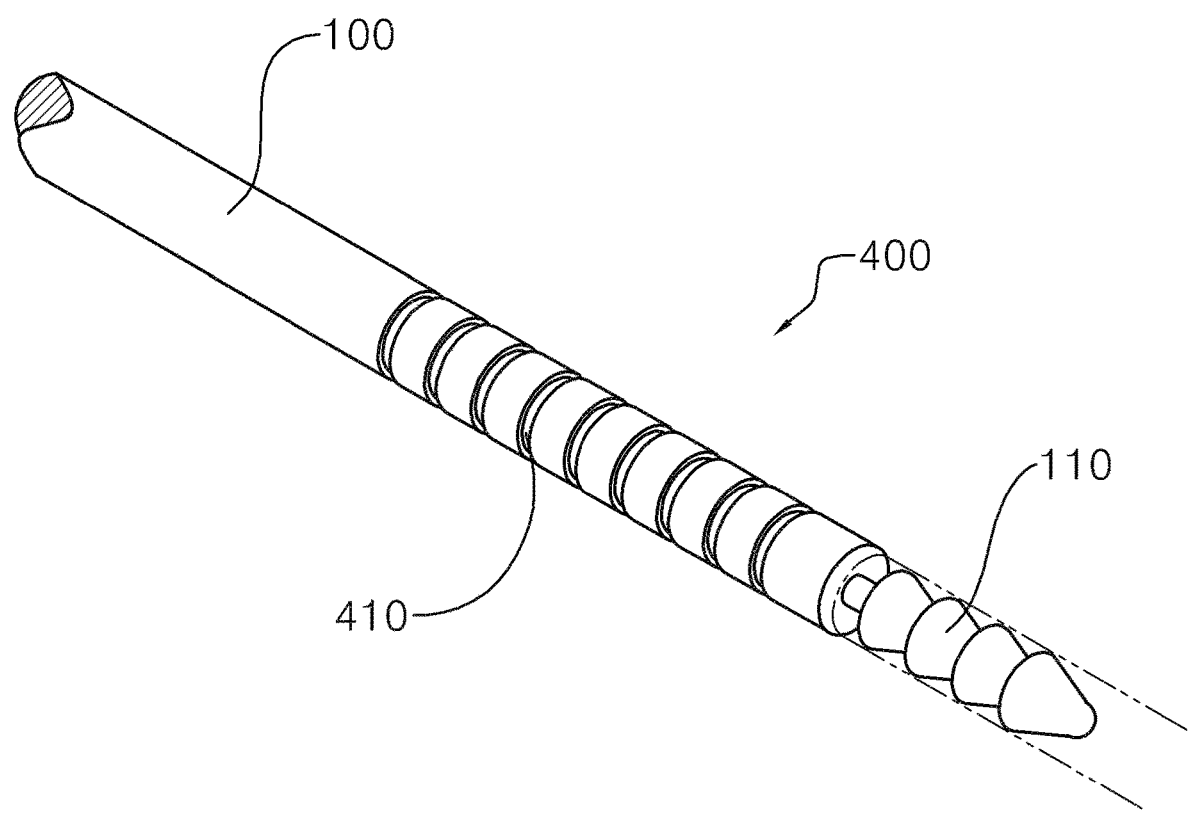
FIG. 16 shows the handle portion having a plurality of concavo-convex parts according to a second embodiment of the present invention.
Figure 17:
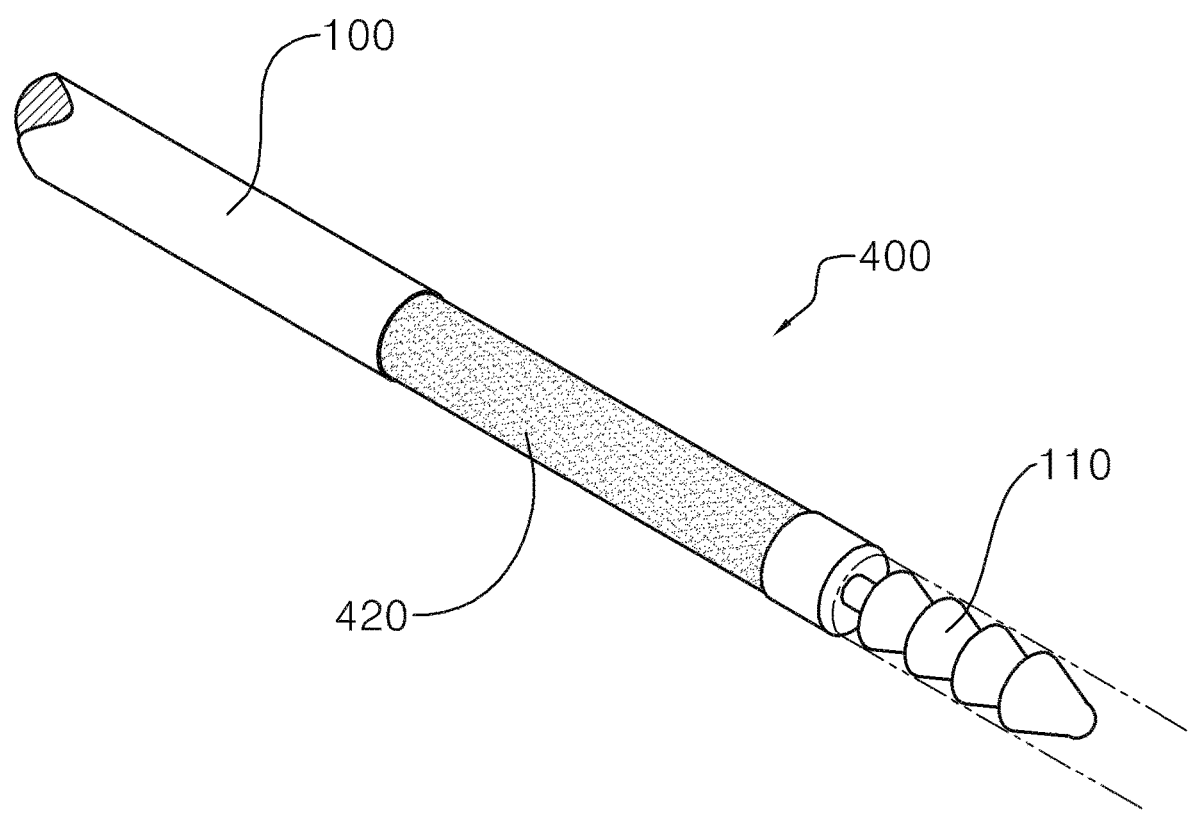
FIG. 17 shows the handle portion having an adhesion layer according to a third embodiment of the present invention.

In another embodiment of the present invention, as shown in FIG. 14, the handle portion 400 may be integrally formed with a predetermined inward portion of the rear end 110 of the needle 100, other than coupling a separate fixing handle 200 to the needle 100. The handle portion 400 may have a concavo-convex part 410 arranged in the form of an embossed shape as shown in FIG. 15, or may have a concavo-convex part 410 formed by carving a groove around the needle as shown in FIG. 16. In addition, as shown in FIG. 17, an adhesion layer 420 formed by applying the adhesion material may be used as a device for increasing the frictional force, so that the operator can stably guide the tube 300 coupled to the rear end 110 into the body without slipping when holding the handle portion 400.

In order to minimize the tissue damage of the skin during the penetration of the needle 100, it is preferred that the diameter of the handle portion 400 is slightly smaller than the diameter of the needle 100 while the handle portion 400 is provided with the concavo-convex part 410 or the adhesion layer 420, other than forming the handle portion 400 to protrude more than the surface of the needle 100.

Although the present invention has been described with reference to the embodiments thereof, it will be understood that various modifications can be made without departing from the spirit and scope of the present invention.

| [Description of Reference numerals] | |
|---|---|
| 100: Needle | 110: Rear end |
| 120: Coupling part | 121: Coupling groove |
| 200: Fixing handle | |
| 210, 210': Upper and lower bodies | |
| 220: Coupling protrusion | 230: Hinge part |
| 240: Coupling-fixing device | 260: Coupling guide groove |
| 270: Coupling space | 280: Antislip device |
| 281: Concavo-convex part | 282: Adhesion layer |
| 300: Tube | 400: Handle portion |
| 410: Concavo-convex part | 420: Adhesion layer |

The invention claimed is:

1. A guiding needle for a suction tube, the guiding needle comprising:
   a rear end coupled to one end of a tube connected to a drainage container for discharging body blood of a patient;
   a coupling part provided at an inward of the rear end of the needle; and
   a fixing handle detachably coupled to the coupling part, wherein the coupling part includes a coupling groove formed on an outer circumference of the needle, and a coupling protrusion is provided at an inner side of the fixing handle so as to be inserted into the coupling groove.

2. The guiding needle of claim 1, wherein the coupling groove includes an elongated groove formed in a longitudinal direction of the needle.

3. A guiding needle for a suction tube, the guiding needle comprising:
   a rear end coupled to one end of a tube connected to a drainage container for discharging body blood of a patient;
   a coupling part provided at an inward of the rear end of the needle; and
   a fixing handle detachably coupled to the coupling part, wherein the coupling part has one of circular, elliptical, and polygonal sectional shapes, and the fixing handle fitted to the coupling part has one of circular, elliptical, and polygonal inner sectional shapes corresponding to the sectional shape of the coupling part.

4. A guiding needle for a suction tube, the guiding needle comprising:
   a rear end coupled to one end of a tube connected to a drainage container for discharging body blood of a patient;
   a coupling part provided at an inward of the rear end of the needle; and
   a fixing handle detachably coupled to the coupling part, wherein the fixing handle is divided into upper and lower bodies, has a hinge part on one side of the upper and lower bodies, and has a coupling-fixing device on an opposite side of the hinge part.

5. The guiding needle of claim 4, wherein the coupling-fixing device includes magnetic members attractive to each other by a magnetic force.

6. The guiding needle of claim 4, wherein the coupling-fixing device is formed in a latch shape so as to be latched.

7. A guiding needle for a suction tube, the guiding needle comprising:
   a rear end coupled to one end of a tube connected to a drainage container for discharging body blood of a patient;
   a coupling part provided at an inward of the rear end of the needle; and
   a fixing handle detachably coupled to the coupling part, wherein the fixing handle has a coupling space into which the needle is elastically fitted through a coupling guide groove defined by opening one side of a single body of the fixing handle.

8. A guiding needle for a suction tube, the guiding needle comprising:
   a rear end coupled to one end of a tube connected to a drainage container for discharging body blood of a patient;
   a coupling part provided at an inward of the rear end of the needle;
   a fixing handle detachably coupled to the coupling part; and
   an antislip device provided on upper and lower contact surfaces of the fixing handle.

9. The guiding needle of claim 8, wherein the antislip device includes a plurality of concavo-convex parts.

10. The guiding needle of claim 8, wherein the antislip device includes an adhesion layer having a surface coated with an adhesion material.

11. A guiding needle for a suction tube, the guiding needle comprising:
    a rear end coupled to one end of a tube connected to a drainage container for discharging body blood of a patient; and
    a handle portion integrally formed with a predetermined inward portion of the rear end of the needle.

12. The guiding needle of claim 11, wherein the handle portion includes a plurality of concavo-convex parts formed on a surface of the needle.

13. The guiding needle of claim 11, wherein the handle portion includes an adhesion layer formed by applying an adhesion material to a surface of the needle.

* * * * *